United States Patent [19]

Torres

[11] 4,309,899
[45] Jan. 12, 1982

[54] EQUIPMENT HOLDER

[75] Inventor: Carlos A. Torres, Brookshire, Tex.

[73] Assignee: McMurry/Hughes, Inc., Huntsville, Tex.

[21] Appl. No.: 26,609

[22] Filed: Apr. 3, 1979

[51] Int. Cl.³ .......................................... G01N 17/00
[52] U.S. Cl. ................................................... 73/86
[58] Field of Search ........................................ 73/86

[56] References Cited

U.S. PATENT DOCUMENTS

| | | | |
|---|---|---|---|
| 2,752,228 | 6/1956 | Gould | 73/86 |
| 2,783,644 | 3/1957 | Willis | 73/86 |
| 4,179,920 | 12/1979 | Schuller et al. | 73/86 |

Primary Examiner—S. Clement Swisher
Attorney, Agent, or Firm—Robert A. Felsman

[57] ABSTRACT

Disclosed is a holder which may be used for mounting equipment, such as sensing apparatus, within an otherwise closed environment. The holder is anchored and sealed to a landing device and may extend a mounting section into the interior of such a container. The mounting section is releasably attached to a seal section of the holder, which is selectively oriented by cooperation between an orienting device, fixed to the seal section, and a contoured surface within the landing device. The seal section is connected to an anchor section of the holder by a projection of the seal section into the anchor section. A washer spring operates as a clutch between the seal and anchor sections.

48 Claims, 7 Drawing Figures

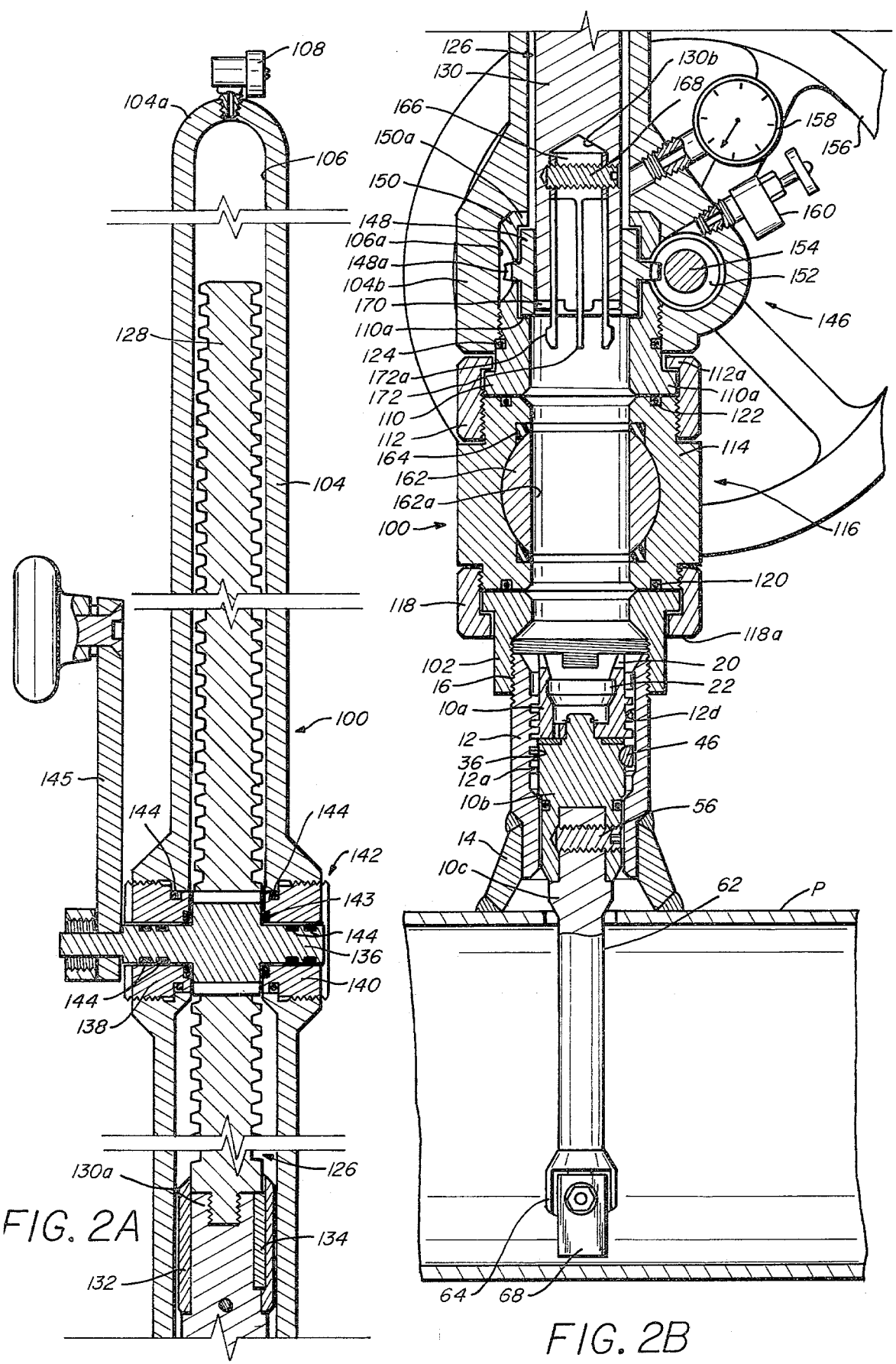

EQUIPMENT HOLDER

BACKGROUND OF THE INVENTION

1. Field of the Invention

The present invention pertains to apparatus for gaining access to the interior of containers. More particularly, the present invention is related to holders for mounting equipment such as sensing or measuring devices within high pressure containers, and tools for inserting and retrieving such holders without exposing the interior of the container to the surrounding atmosphere. Such apparatus is particularly applicable to high pressure fluid pipelines whereby sensors, such as corrosion or scale testing coupons, may be inserted into the fluid flow and retrieved therefrom without shutting down the pipeline flow.

2. Description of the Prior Art

In various industrial settings, it is often necessary to test or sample material under pressure in a pipeline or other enclosure. Access to such material may conceivably be had by first relieving the pressure, or shutting down the flow in the pipeline. This may be a difficult or dangerous procedure, and will usually be expensive. Retrieval tools, or retractors, are known for inserting holders or other fittings through a hole, for example, in the side of a pipe member without the need for shutting down the high pressure pipeline flow. The retrieval tools are also used to withdraw the holders from the pipeline without losing pipeline pressure.

While the holder is in position extending into the interior of the pipeline, a seal is maintained between a fitting mounted on the pipeline and the holder, or equipment attached thereto. During the removal of the holder from the pipeline, continuous sealing to maintain the pipeline pressure must be carried out. The holder must be capable of being totally withdrawn from the pipeline to allow access to testing equipment mounted on the holder for insertion within the pipeline. Thus, the fitting secured to the pipeline must be provided with a valve or other closure device to seal off the pipeline in the absence of the holder.

According to some prior art practices, a valve such as a gate valve is permanently installed on a fitting attached to the pipeline to selectively open and close communication to the tap hole in the side of the pipe. To install a holder extending into the pipeline a retrieval tool is secured and sealed to the valve housing with the holder positioned within the retrieval tool. The valve is opened and the retrieval tool is operated to advance the holder through the valve passage toward the pipeline. The procedure is generally reversed to retrieve the holder from the pipeline.

One type of retrieval tool must remain sealed to the valve housing as long as the holder is in position extending into the pipeline. In such case, the integrity of the sealing of the pipeline pressure is maintained by seal members carried by the retrieval tool rather than the holder.

In another type of tool, the holder may be sealed to fittings attached to the pipeline, and the retrieval tool removed. However, movement of the holder toward or away from the pipeline in the latter case is effected by moving a rod, to which the holder is attached, through a packing gland. A pressure differential across the packing gland may result in unintended movement of the rod.

Advancement of the holder according to prior art apparatus is generally achieved by rotating a screw device to which the holder is attached. Such rotation makes difficult the use of a metal-to-metal seal between the holder and the pipeline fittings. Another disadvantage of such rotation of the holder is the difficulty in providing the exact alignment within the pipeline of the equipment mounted on the holder. For example, where material testing samples, or coupons, are being placed within a high pressure fluid flow, the effect on the testing material may be altered depending on the orientation of the coupon relative to the direction of fluid flow. Generally, where scaling effects are to be determined, the coupon which is laminar in shape is placed with a flat side perpendicular to the direction of flow. For corrosion testing, coupons are placed parallel to the flow direction. Where the holder is advanced solely by a screw action, the orientation of attached coupons will be determined by the final position of the holder relative to the pipeline fittings. Even where additional orientation adjustments to the holder and attached coupons may be made, such adjustments may be difficult and dangerous operations due to the high pressure within the pipeline. Furthermore, since the operator cannot see the coupon, he must depend on fiducial marks on the holder if exposed, or on the retrieval tool.

Another type combination retrieval tool and holder is known whereby the holder may be secured and sealed to a fitting on the pipeline without the need for a permanent valve installation. To insert or to remove the holder a valve is connected to the pipeline fitting, and the retrieval tool is sealed to the top of the valve housing. The valve is opened and the retrieval tool is operated to advance a rod through the valve passage to either insert or retrieve the holder. Again, advancement of the holder is effected by rotating the rod to which the holder is attached. Thus, as discussed hereinbefore, a metal-to-metal seal between the holder and the pipeline fitting is difficult to obtain. Also, the holder and attached coupons must be oriented after the holder is sealed to the pipeline fitting. In this particular type of tool, rotation of the rod to advance or retract the holder is effected by turning an exterior sleeve of the tool.

Gaining access to the interior of a high pressure pipeline may be dangerous, particularly where such procedure is carried out manually. Consequently, it is highly desirable that retrieval tools and holders be designed to maximize safety and ease of use. The uncertainty of the orientation of the equipment positioned within the pipeline may be removed by a holder which is automatically oriented as desired when finally positioned on the pipeline.

Copending United States Patent Application Ser. No. 1,224 filed Jan. 5, 1979 now U.S. Pat. No. 4,275,592 discloses an extractor tool and a holder which may be advanced or retracted by operation of a placement member within the extractor tool. Generally, translational movement and rotational movement may be imparted to the placement member independently by means of two gear boxes at the disposal of the operator. The extractor tool incorporates a valve through which the holder may be passed in either a retrieval or insertion operation. During retrieval, the holder may be withdrawn clear of the valve, and the extractor tool broken above the closed valve to allow access to the holder. The extractor tool may then be reassembled, the valve opened, and the holder returned through the valve to the pipeline.

The holder includes a drive screw which serves to anchor the holder to a landing nipple attached to the pipeline, and a seal section which provides sealing engagement between the holder and the landing nipple. A holder section, on which equipment such as coupons may be mounted, is connected to the seal section. The drive screw is joined to the seal section by a shoulder bolt which permits limited relative translational movement between the drive screw and the seal section, but allows rotational movement therebetween. A clutch is provided to lock the drive screw against rotational movement relative to the seal section. The seal section and/or the attached holder section is equipped with an anchoring or orientation device which engages the landing nipple when the seal section is positioned therein and oriented in a predetermined direction. The anchoring of the seal section against rotation relative to the landing nipple occurs automatically, and thus assures the preferred orientation of equipment attached to the holder. In two embodiments disclosed, the seal section orientation device operates by spring-biasing to engage a detent, or recess, in the interior wall of the landing nipple.

The landing nipple provides an annular, longitudinally extending sealing surface to receive a packing-type seal carried by the seal section. A second seal is provided by contact between complimentary frustoconical surfaces on the landing nipple and the seal section. The drive screw is anchored to the landing nipple by matching low pitch threads. As the drive screw is being rotated by means of the extractor tool to anchor the holder to the landing nipple, the clutch causes the seal section to rotate with the drive screw. When the seal section has been advanced sufficiently in the area of the landing nipple sealing surfaces, the seal section anchor device engages the detent or recess of the landing nipple and the clutch is overridden as the drive screw is further rotated. Thereafter, advancement of the drive screw along the landing nipple threads occurs with rotation of the drive screw but without further rotation of the seal section. The aforementioned metal-to-metal seal provided by the frustoconical surfaces of the landing nipple and the seal section is closed by the drive screw being tightened on the seal section by means of the landing nipple threads.

SUMMARY OF THE INVENTION

The present invention provides an improvement in holders to be secured and sealed to a landing nipple attached to, for example, a high pressure pipeline, and which holders may be, for example, so mounted on a landing nipple circumscribing a hole communicating with the pipeline interior, or removed therefrom, by use of an extractor-type tool.

A holder according to the present invention includes means for anchoring the holder to a landing nipple by threadedly engaging the landing nipple, and means for fluid-sealing the holder to the landing nipple. The anchoring means may be in the form of a drive screw with course threads which engage matching internal threads of the landing nipple. The seal means may include at least one seal element which cooperates with the landing nipple to effect a fluid-tight seal between the holder and the landing nipple. In the embodiment shown herein, a seal section carries an O-ring seal which seals against an interior seal surface on the landing nipple. Also, a metal-to-metal seal is shown effected by the engagement of complimentary frustoconical surfaces of the seal section and of the landing nipple, respectively.

The seal section is coupled to the drive screw by a projection, or shaft, of the seal section passing through one end of the drive screw and into the interior of the drive screw. A retainer is joined to the projection to prevent its withdrawal from the drive screw. However, the shaft is sufficiently long to permit limited longitudinal translational movement between the seal section and the drive screw. This construction eliminates the need for a separate shoulder bolt and simplifies the machining steps required in constructing the holder.

The aforementioned projection-retainer coupling between the seal section and the drive screw permits relative rotational movement therebetween. A clutch mechanism is provided for imparting torque between the drive screw and the seal section. The clutch mechanism is a generally annular compression-type clutch. In the embodiment shown, a spring washer, or wavy washer, is positioned between the seal section and the drive screw, with the seal section shaft passing through the washer and into the drive screw. The length of the shaft is such as to confine the washer between the seal section and the drive screw under compression throughout the permitted range of longitudinal translational motion between the seal section and the drive screw. Such compression is sufficient to cause frictional forces to be generated between the wavy washer and both the seal section and the drive screw. Thus, whenever the drive screw is rotated about its longitudinal axis, the interactions between the drive screw and the wavy washer, and between the wavy washer and the seal section cause torque to be communicated between the drive screw and the seal section by way of the wavy washer. In such case, the seal section will rotate with the drive screw unless force is present to otherwise prevent such rotation of the seal section. This construction, as opposed to one in which the friction clutch is provided by a member rigidly affixed to either the seal section or the drive screw, reduces any tendency of the clutch mechanism to freeze and lock the seal section and drive screw together. As compared with a spring loaded plunger or similar friction creating device, the clutch mechanism of the present invention is less expensive, simpler in construction and operation, and more easily employed in the holder.

Means for automatically orienting the seal section relative to the landing nipple are provided, and include cooperating elements of both the landing nipple and the seal section. When the seal section has been received by the landing nipple to effect a fluid-tight seal therebetween, the orientation elements of both the landing nipple and the seal section are located on the opposite side of at least one seal element from the high-pressure fluid side of the seal. This feature presents the orienting means from becoming gummed up, corroded or otherwise damaged due to prolonged exposure to the material on the high pressure side of the seal.

The orientation elements include an interior contoured surface of the landing nipple which is engaged by an element fixed to the seal section. Movement of the fixed orienting element relative to the seal section is not required. The landing nipple surface aligns and guides the seal section as the holder is inserted within the landing nipple. With the holder anchored and fluid-sealed to the landing nipple, the rotational orientation of the seal section relative to the landing nipple is determined and maintained automatically by the constraint imposed by the contoured surface on the fixed orientation element of the seal section. Orientation is thus obtained without need for springs or spring loaded plungers which may jam or otherwise malfunction. This feature improves the reliability of the orientation procedure and also contributes to a reduction in fabrication costs.

Relative movement between the seal section and the drive screw is also affected by an abutment means which limits the longitudinal translational movement of the seal section and the drive screw toward each other. The extent to which the wavy washer confined between the seal section and the drive screw may be compressed is also thereby limited. In the embodiment shown, the abutment means includes an annular shoulder of the seal section circumscribing the base of the seal section projection. As the seal section and drive screw are brought together, the shoulder eventually abuts, or contacts, the drive screw before the wavy washer is completely collapsed. Thrust may then be communicated directly between the drive screw and the seal section without further compression, and possible damage, of the wavy washer. This feature also prevents bypass openings in the holder from being closed by full surface contact between the ends of the drive screw and the seal section.

Equipment to be mounted on the holder for exposure to the interior of a high pressure pipeline or other container may be supported on mounting apparatus as part of the holder. Such mounting apparatus may be of any convenient and appropriate length to effect the desired placement of the equipment relative to the container when the holder is anchored and sealed to the landing nipple. The mounting apparatus, or holder section, is rigidly attached to the seal section so that, as the seal section is automatically oriented relative to the landing nipple as described hereinbefore, the holder section, along with equipment mounted thereon, is also oriented relative to the container.

To facilitate the possible variation in holder section lengths to accommodate differing applications, the connection between the holder section and the seal section is releaseable. Thus, a holder section of a desired length may be selected from an inventory of holder sections of various lengths and conveniently attached to a seal section. Similarly, a holder section may be relatively quickly and easily removed from a seal section and replaced with a holder section of different length.

The holder section may be equipped with insulation to isolate the metal portions of the holder section from the equipment mounted thereon. Thus, for example, dissimilar metal reactions between the holder section and, say, a testing coupon may be avoided by interposing insulation therebetween. The coupon may be held to the holder section by a nut and bolt, with a teflon lining, for example, sandwiched between the coupon and the metal of the holder section. A flanged teflon sleeve may also circumscribe the bolt to insulate it from the coupon. A shoulder formed on the holder section cooperates with a shoulder on the insulator to hold a flat topped member fixed relative to the holder section with the use of only one nut and bolt.

A holder according to the present invention may be inserted, anchored and sealed in a landing nipple by means of an extractor tool of the type disclosed in aforementioned patent application Ser. No. 1,224. It may also be operated with any device such as a hot-tap tool, which provides the necessary rotational and translational movements.

BRIEF DESCRIPTION OF THE DRAWINGS

FIGS. 2A and 2B together comprise a side elevation in partial section of an extractor tool joined to the landing nipple securing the coupon holder of FIG. 1 to the pipe, with FIG. 2A showing the top of the tool and FIG. 2B showing the bottom of the tool and the coupon holder;

DESCRIPTION OF PREFERRED EMBODIMENT

Figure 1:
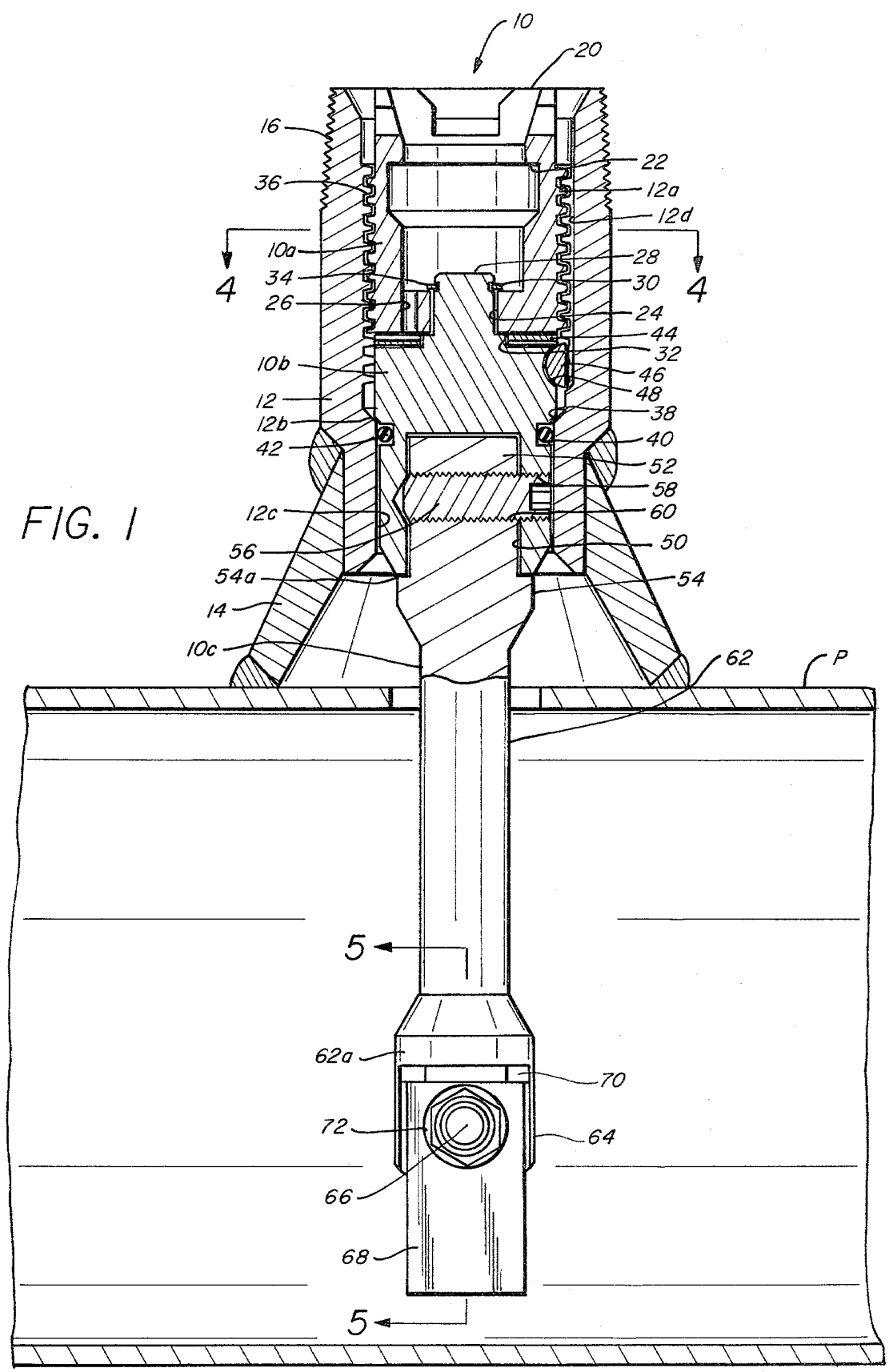
FIG. 1 is a side elevation in partial section of a coupon holder according to the present invention, extending in operating position within a pipe.
Figure 4:
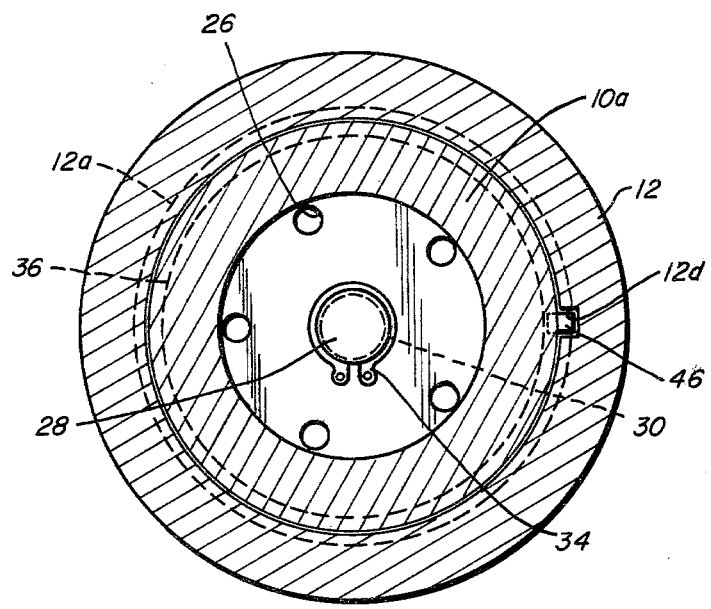
FIG. 4 is a horizontal cross-sectional view taken along line 4—4 of FIG. 1 and showing five bypass ports.
Figure 5:
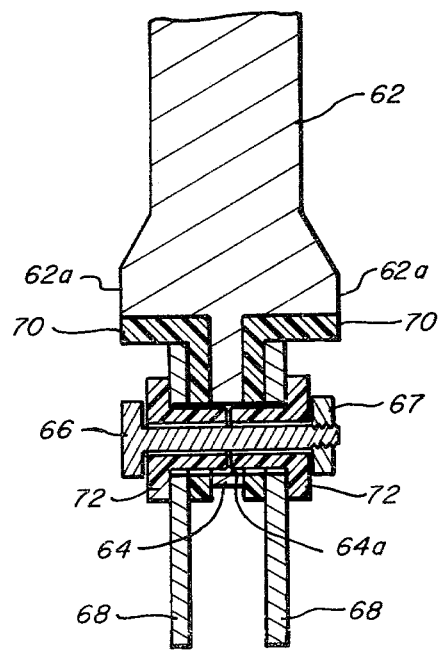
FIG. 5 is a vertical cross-sectional view, taken along line 5—5 of FIG. 1, of a fragment of the holder section illustrating the construction of the holder section insulation.

A holder according to the present invention is shown generally at 10 in FIG. 1 secured in operating position, extending through a tap hole in a pipe member P, by means of a landing nipple 12. Details of the holder 10 are shown in FIGS. 4 and 5. While the landing nipple may be designed to be fixed directly to the pipe member P, the nipple is shown welded to a flared base 14 which is welded directly to the pipe. The holder at 10 includes three general sections: a drive screw 10a; a seal section 10b; and a mounting, or holder, section 10c. The drive screw 10a fixes the holder to the landing nipple 12 against longitudinal movement relative thereto. The seal section 10b seals the holder to the landing nipple 12 and, therefore, to the pipe P. The construction and function of the various sections of the holder 10 are discussed in detail hereinafter. The holder section 10c illustrated and described herein is capable of receiving and supporting testing coupons, although other types of equipment may be supported by means of the present invention.

With the holder 10 positioned and secured within the landing nipple 12, a cap (not shown) may be used to close the exterior open end of the nipple as described in the aforementioned U.S. patent application Ser. No. 1,224. The cap is threadedly engaged to the landing nipple by external nipple threads 16 which also serve a purpose discussed hereinafter. Thus, the cap not only covers the top of the holder 10, but also protects the aforementioned threads 16.

The drive screw 10a of the holder 10 is generally tubular in construction. The top end of the drive screw 10a is scalloped to form a plurality of upwardly extending projections, or rotary screw dogs, 20. An undercut shoulder 22 is formed within the drive screw 10a just below the dogs 20. The dogs 20 and the shoulder 22 serve purposes discussed hereinafter.

The bottom of the drive screw 10a is closed except for a longitudinally extending throughbore 24 centered along the cylindrical axis of the drive screw, and at least one bypass port 26. As seen in FIG. 5, five bypass ports 26 are included in the holder 10.

The top of the seal section 10b ends in a longitudinally extending shaft 28 centered along the cylindrical axis of the seal section and featuring an annular groove 30. The base of the shaft 28 is surrounded by an annular shoulder 32.

The drive screw 10a is connected to the seal section 10b by means of the shaft 28 protruding upwardly through the bore 24 into the interior of the drive screw. A retainer in the form of a snap ring 34 is positioned within the groove 30 to extend beyond the transverse dimension of the bore 24 and be stopped by the bottom of the drive screw 10a to prevent the shaft 28 from being withdrawn through the bore. The shoulder 32 also extends beyond the transverse dimension of the bore 24 to limit the relative upward movement of the seal section 10b toward the drive screw 10a. The distance along the shaft 28 between the top of the shoulder 32 and the bottom of the snap ring 34 is greater than the thickness of the bottom of the drive screw 10a along the bore 24. Thus, the length of the shaft 28 between the shoulder 32 and the snap ring 34, compared to the length of the drive screw bore 24, permits limited longitudinal translational movement between the drive screw 10a and the seal section 10b, while the snap ring maintains the drive screw and the seal section joined together. The use of a snap ring 34 and groove 30 is not per se a part of the present invention but is intended to be illustrative of one embodiment of the invention whereby means are provided for securing the drive screw 10a to the seal section 10b.

The external surface of the drive screw is equipped with course, low pitch threads 36 which mesh with corresponding threads 12a along the interior of the landing nipple 12. The interior of the landing nipple is reduced in diameter below the threads 12a, with the change in lateral dimension of the nipple interior marked by an upwardly facing frustoconical annular shoulder 12b. The seal section 10b generally features a reduction in outer diameter marked by a downwardly facing frustoconical annular shoulder 38. The two shoulders 12b and 38 have complementary angles of taper. Thus, with the seal section 10b pressed firmly downwardly relative to the landing nipple, as discussed more fully hereinafter, the two shoulders 12b and 38 form a metal-to-metal seal between the coupon holder and the landing nipple.

The seal section 10b carries, in an appropriate groove 40, resilient packing material 42 which engages the landing nipple interior surface 12c below the shoulder 12b. The surface 12c, which may be polished, acts as a seat to receive the packing 42 to provide a primary seal between the seal section 10b and the landing nipple 12. The packing material 42 may be of any suitable composition and construction, including an O-ring. The O-ring seal, rather than the metal-to-metal seal is intended to function as the primary seal in the system since the O-ring may be easily replaced and the metal-to-metal seal may not completely seal due to surface defects which occur with use.

A friction clutch, in the form of a spring washer, or wavy washer, 44, provides a further engagement between the drive screw 10a and the seal section 10b. With the drive screw 10a and the seal section 10b connected by means of the shaft 28 and the snap ring 34 as discussed hereinbefore, the washer 44 is confined between the lower face of the drive screw and the upper face of the seal section, generally circumscribing the seal section annular shoulder 32.

As noted hereinbefore, the length of the shaft 28 between the shoulder 32 and the snap ring 34 permits limited longitudinal translational movement between the drive screw 10a and the seal section 10b. With the seal section 10b withdrawn from the drive screw 10a to the extent permitted by the snap ring 34, the washer 44 is still compressed between the drive screw and the seal section. As the seal section 10b and the drive screw 10a are brought closer together, the washer 44 is further compressed. Throughout the range of the permitted relative translational movement between the seal section 10b and the drive screw 10a, the washer 44 maintains sufficient surface contact with both the drive screw 10a and the seal section 10b, under pressure due to the inherent spring biasing of the washer to generate frictional forces between the washer and the drive screw, and between the washer and the seal section. By means of such forces the washer 44 provides a torque-transmitting connection between the drive screw 10a and the seal section 10b. Consequently, rotation of the drive screw 10a about its longitudinal axis imparts torque to the washer 44, and therefore, to the seal section which will also rotate in the absence of torque acting on the seal section to nullify the washer-transmitted torque.

The extent to which the spring washer 44 is compressed depends on the relative longitudinal positions of the drive screw 10a and the seal section 10b. The abutment of the seal section shoulder 32 against the bottom of the drive screw 10a prevents the complete collapse of the washer 44 between the seal section 10b and the drive screw.

The interior landing nipple threads 12a are interrupted by a longitudinal slot 12d whose depth is greater than that of the roots of the threads 12a. A semicircular key 46 is positioned in an arcuate slot 48 cut in the side of the seal section 10b. The shape of the slot 48 matches that of an arcuate portion of the key 46. The key 46 may be soldered in place in the slot 48 and thereby held fixed relative to seal section 10b with the flat edge of the key extending beyond the surface of the seal section. As shown in FIG. 1, the key 46 also extends beyond the radially inner limit, or roots, of the landing nipple threads 12a.

With the seal section 10b positioned within the landing nipple with the key 46 within the longitudinal extent of the threads 12a, the rotational orientation of the seal section is constrained by the key being confined to the slot 12d. Thus, rotation of the seal section 10b about its longitudinal axis is prevented by the confinement of the key 46 within the longitudinal slot 12d. While the key and groove configuration are not, per se, a part of the present invention, they are illustrative of an embodiment of the invention which employs an orientation means which is fixed relative to the seal section 10b and cooperates with a contoured surface in the nipple to provide the desired orientation of the seal section.

The bottom of the seal section 10b features a downwardly facing bore 50 whose longitudinal axis is coincidental with that of the seal section. The bore 50 receives the cylindrical upper end 52 of the holder section 10c. An annular flange 54 provides an upwardly facing shoulder 54a defining the bottom of the cylindrical end 52. The orientation and alignment of the holder section 10c relative to the seal section 10b may be fixed with the cylinder 52 inserted in the bore 50 by the shoulder 54a held firmly against the bottom of the seal section surrounding the bore 50. A set screw 56 is threaded in lateral bores 58 and 60 in the seal section 10b and the holder section 10c, respectively, to anchor the holder section with the shoulder 54a against the seal section bottom. Then, the rotational orientation of the holder section 10c is also constrained by the key 46 being confined to the slot 12d. The specific means of a set screw 56 and bore 50 are not, per se, a part of the present invention but are intended only to be illustrative of one embodiment of the invention whereby means are provided for changing the equipment attached to the seal section 10b.

The holder section 10c also includes a shaft 62 and a tab-shaped base 64. As shown in FIG. 5, the tab 64 of the holder section 10c may receive a coupon on either side thereof. A hole 64a is provided in the tab 64 for receiving a bolt 66 to secure the coupons to the holder section 10c. The bolt 66 is secured by a nut 67. A pair of coupons 68 is shown held to the tab 64 in FIG. 5, although a single coupon may be used at a time. Coupons are generally flat material samples, and may readily be applied to the coupon holder 10 in this manner. With the coupons held parallel to the tab of the holder section 10c, their orientation is determined by that of the holder section. Further, the rotational orientation of the holder section 10c is determined by that of the seal section 10b. Confinement of the key 46 in the slot 12d limits the rotational orientation of the seal section 10b in operating configuration, as indicated by FIG. 1, to that which aligns the tab 64 of the holder section 10c and, therefore, any coupons attached thereto with the longitudinal direction of the pipe P. Consequently, any coupons, such as 68, placed in the pipe on the holder section 10c will be oriented so that fluid flow through the pipe will be along the flat surfaces of the coupons with an edge of each coupon facing upstream. In practice, this is the generally preferred orientation for such coupons used in corrosion testing, as noted hereinbefore. However, it will be appreciated that any orientation of the coupon may be effected, for example, by moving the location of the key 46 to a different rotational position on the seal section 10b, or by changing the rotational position of the landing nipple slot 12d. The orientation of the coupons may also be altered by changing the rotational orientation of the holder section 10c relative to the seal section 10b. Such a change may be accomplished by changing the rotational position of the seal section threaded bore 58, or that of the holder section threaded bore 60.

The holder section 10c, including the tab 64, may be constructed of stainless steel or some other metallic material featuring good corrosion resistance. The testing coupons are generally metallic as well. To avoid possible galvanic effects from contact between the dissimilar metals of the holder section 10c and the coupons 68, a non-metallic insulating lining may be provided. Appropriate insulating material such as teflon, rubber or plastic may be used for this purpose, depending on the characteristics of the fluid in the pipeline.

As best seen in FIG. 5, the holder section shaft 62 broadens to form a pair of downwardly facing shoulders 62a which flank the top of the tab 64. A pair of L-shaped insulation inserts 70 fit against the tab 64 and each of the shoulders 62a. The coupons 68 are held in place against the inserts 70 and, therefore, fixed to the tab 64 by the bolt 66 and nut 67, with the bolt passing through appropriate holes in the inserts as illustrated. A pair of insulating flanged sleeves 72 surround the bolt 66 and line the holes in the coupons 68, in the inserts 70 and in the tab 64 through which the bolt passes to complete the isolation of the shoulders 62a and the tab from the coupons. The flanges of the sleeves 72 isolate the head of the bolt 66 and the nut 67 from the coupons 68 as shown in FIG. 5. Thus, the bolt 66 and nut 67, which may also be made of stainless steel, are isolated from the coupons 68 as well.

A single coupon 68 may be mounted on the holder section 10c and isolated from the tab 64, bolt 66 and nut 67 by using one sleeve or both insulating sleeves with shorter shanks.

The alignment of the coupons 68 relative to the holder section 10c is secured by the squared top of each coupon being placed evenly against the top portion or shoulder of the corresponding insulating insert 70. Thus, the coupons 68 are rigidly joined to the holder section 10c, without need for more than a single bolt. The inserts 70 also function such that the metal parts of the holder section are isolated from direct contact with the coupon.

In its operating configuration (FIG. 1), the coupon holder 10 is held firmly within the nipple 12 by the drive screw 10a advanced as far as it can go along the threads 12a of the landing nipple 12. Thus, the drive screw 10a abuts the shoulder 32 and presses down against the seal section 10b, maintaining surfaces 12b and 38 of the nipple 12 and seal section, respectively, in fluid-sealing engagement. The primary seal is established between the packing 42 and the seating surface 12c of the nipple 12. Also, the key 46, being confined to the slot 12d, defines the orientation of the tab 64 and, therefore, the orientation of the coupons 68 relative to the direction of fluid flow within the pipe P.

As noted hereinbefore, and as described in the aforementioned copending patent application, a protective cap may be be used to close the top of the landing nipple 12 with the coupon holder 10 in the operating configuration of FIG. 1. The coupon holder 10 may be placed in this operating configuration on a pipe containing a fluid under pressure, or removed therefrom, by use of an extractor tool such as the one disclosed in that patent application. To fully describe the operation of the coupon holder 10, a description of that extractor tool and its use with the present invention is provided herein.

The extractor tool is shown generally at 100 in FIGS. 2A and 2B coupled to the landing nipple 12 by a floating nut 102 engaging the external landing nipple threads 16.

The tool 100 includes an elongate housing 104 defining an inner chamber 106 that extends the length of the housing. One end of the housing 104a is closed except for a bleed valve 108 which may be used to selectively open a leak path to the environment. The opposite end of the housing 104b is enlarged in transverse dimension to include a portion of the inner chamber 106a of increased transverse dimension compared to the remainder of the chamber 106.

A worm gear retainer 110 extends into the enlarged chamber area 106a and threadedly engages the end of the housing 104b. The end of the worm gear retainer 110 external to the housing 104 features a radially outwardly extending flange 110a which is overlapped by a radially inwardly extending flange 112a of a nut 112. The nut 112 threadedly engages the housing 114 of a ball valve shown generally at 116. Similarly, the upper end of the floating nut 102 features a radially outwardly extending flange 102a which is overlapped by a radially inwardly extending flange 118a of a nut 118. The latter nut 118 threadedly engages the ball valve housing 114.

With the nuts 112 and 118 tightened on the valve housing 114, the worm gear retainer 110 and the floating nut 102, respectively, are held fixed relative to the valve housing 114. Therefore, with the threaded engagement between the worm gear retainer 110 and the housing 104 tightened, the entire extractor tool is secured to the landing nipple, and, therefore, to the pipe P. O-ring seals 120 and 122 fluid-seal the floating nut 102 and the worm gear retainer 110, respectively, to the valve housing 114. An O-ring seal 124 fluid-seals the worm gear retainer 110 to the housing 104. The floating nut 102 may be sufficiently tightened on the threads 16 of the landing nipple 12 to effect a fluid-tight engagement therebetween. Thus, with the cooperation of additional sealing described hereinafter, the inner chamber 106 may communicate with the interior of the landing nipple 12 by way of the ball valve at 116, without fluid communication to the environment surrounding the extractor tool 100 and the pipe P.

A placement member, shown generally at 126, is positioned within the housing 104 for movement along the chamber 106. The placement member 126 includes a cylindrical rack 128 and a torque head 130 joined together by a threaded connection. A spline collar 132 is received over a section 130a of reduced diameter of the torque head 130 at the threaded junction with the rack 128, and is locked against rotational movement relative to the torque head by a key 134 received in appropriate grooves in both the torque head and the spline collar. With the rack 128 joined to the torque head 130 as shown, the spline collar 132 is fixed against rotational and longitudinal movement relative to both the rack and the torque head by the key 134 and appropriate shoulders.

The placement member 126 may be selectively moved along the inner chamber 106 by rotation of a spur gear 136 with which the cylindrical rack 128 is meshed. The spur gear 136 is positioned between two gear retainers 138 and 140 which are joined by threaded connection to the housing 104 at an enlarged offset portion thereof to form a first gear box indicated generally at 142. The spur gear 132 rides on thrust bearings 143 positioned in annular grooves in both gear retainers 138 and 140. O-ring seals 144 are provided to fluid-seal the shaft of the spur gear to both gear retainers, and to seal the retainers to the housing 104. One end of the spur gear shaft carries a crank handle 145 by which the spur gear 136 may be selectively rotated.

A second gear box, indicated generally at 146, is formed at the enlarged end of the housing 104b. A worm gear 148 rides on a radially inwardly extending shoulder 110a of the worm gear retainer 110. A collar 150 is equipped with a radially inwardly extending flange 150a to further prevent longitudinal movement of the worm gear 148 along the enlarged chamber area 106a.

The worm gear 148 features a ring of radially outwardly extending teeth 148a which mesh with a helical gear 152 carried on a shaft 154. The helical gear 152 and shaft 154 are positioned in an appropriate throughbore in the wall of the enlarged housing end 104b. A second crank handle in the form of a wheel 156 is fixed to the shaft 154 to control rotational motion thereof. Then, rotation of the wheel 156 causes rotation of the helical gear 152 which is fixed against rotation relative to the shaft 154.

Both the collar 150 and the gear retainer 110 are tapered toward the worm gear 148 as shown to accommodate the helical gear 152 and the shaft 154. However, both tapered ends of elements 110 and 150 may contact the worm gear 148 at the teeth 148a to provide additional support for the worm gear.

As the helical gear 152 is rotated, interaction between this gear and the teeth 148a of the worm gear causes rotation of the worm gear 148 about its axis of cylindrical symmetry, which is essentially conincidental with the longitudinal axis of the inner chamber 106. The interior of the worm gear 148 features a plurality of radially inwardly extending splines which mesh with an equal number of radially outwardly extending splines on the spline collar 132. However, such engagement between the worm gear 148 and the spline collar 132 occurs only when the placement member 126 is positioned along the inner chamber 106 so that the spline collar overlaps the worm gear. This is the case in FIGS. 3A and 3B wherein the placement member 126 is shown in a lowered position and engaging the coupon holder 10.

It will be appreciated that engagement of the spur gear 136 with the rack 128 may be used to provide translational movement of the placement member 126 along the inner chamber 106, while engagement of the worm gear 148 with the spline collar 132 may be used to provide rotational motion of the placement member about its longitudinal axis. However, such engagement between the spur gear 136 and the rack 128 does not prevent the placement member 126 from being rotated. Similarly, such engagement between the worm gear 148 and the spline collar 132 does not prevent translational movement of the placement member along the inner chamber 106.

A pressure gauge 158 and a bleed valve 160 are secured to the wall of the enlarged housing end 104b, and communicate, by way of appropriate passages therethrough, to the interior of the housing 104. The gauge 158 and the valves 108 and 160 are tightened in their respective threaded holes in the housing 104 to provide fluid-tight sealing. Similarly, the shaft 154 may ride on bearings secured, in conventional manner, by retainers (not shown) joined to the housing end 104b, and be fluid-tight sealed ultimately to the housing at 104. Thus, the integrity of the fluid-tight sealing of the inner chamber 106 is preserved by the seals and fittings provided at the first gear box 142 as well as the second gear box 146.

The ball valve at 116 includes a valve element 162 with a central passage 162a of approximately the same diameter as that of the inner chamber 106. Appropriate packing rings 164 are provided to seal the valve element 162 to the valve housing 104. The valve 116 may be selectively opened or closed by operation of a handle (not shown). The handle is fixed to a shaft (not shown) extending through the housing 114 and engaging the valve element 162 in conventional fashion. Rotation of the handle 90° causes rotation of the valve element 162 to close the valve 116.

Figures 3A, 3B:
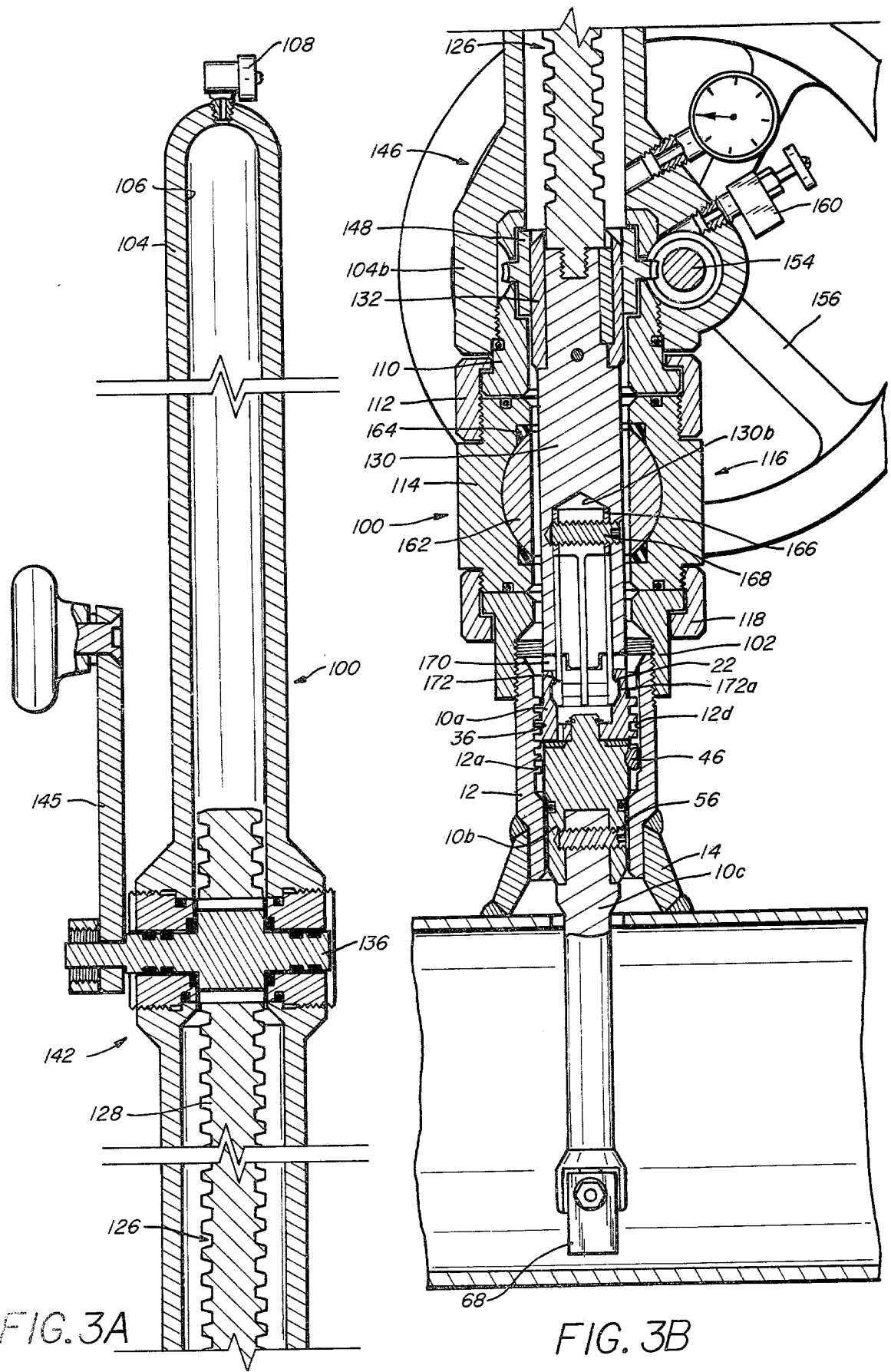
FIGS. 3A and 3B together are side elevations in partial section similar to FIGS. 2A and 2B together, with the placement member of the tool engaging the coupon holder.

The worm gear retainer 110, the ball valve housing 114, and the floating nut 102 also provide interior passages therethrough corresponding in cross section to the inner chamber 106. Thus, the placement member 126 may be moved through the valve, in open configuration, and out through the floating nut 102. The spline collar 132 is closely confined against lateral movement upon engagement with the worm gear 148. Thus, rotation of the spur gear 136 in the appropriate rotational sense may be used to lower the placement member 126 to engage the holder 10 as shown in FIGS. 3A and 3B.

The lower end of the torque head 130 features an upwardly extending recess 130b. A collet assembly 166 is positioned within the recess 130b and held therein by a set screw 168 secured within an appropriate threaded hole in the side of the torque head 130.

As may be seen in FIG. 2B, the end of the torque head 130 is scalloped to form a plurality of downwardly extending projections, or rotary drive dogs, 170. A plurality of collet fingers 172 of the assembly 166 extends downwardly beyond the rotary drive dogs 170, and ends in radially outwardly facing latches 172a. The collet fingers 172 are formed biased radially outwardly.

The holder 10 of the present invention may be retrieved from its operating configuration illustrated in FIGS. 1 and 2B by use of the extractor tool 100 as follows. This procedure may be appreciated by reference to FIGS. 3A and 3B.

With the extractor tool 100 mounted on the landing nipple 12 as described and shown in FIGS. 2A and 2B, and with the ball valve 116 in open configuration as shown, the first crank handle 145 is rotated in the appropriate rotational sense to drive the rack 128 downwardly by way of the spur gear 136. Thus, the placement member 126 is lowered within the inner chamber 106. When the bottom of the spline collar 132 reaches the top of the worm gear 148, the splines of these two elements may be meshed. The second crank handle 156 may be turned to rotate the worm gear 148 as needed to align the splines of collar 132 with the spaces between the splines of the worm gear. Then, the placement member 126 may continue to be lowered without rotation, by operation of the first handle 145 as the spline collar 132 slides along within the worm gear 148.

As the placement member 126 continues to be lowered, the collet fingers 172 pass down within the interior of the drive screw 10a. The rotary drive dogs 170 of the torque head 130 may be made to mesh with the dogs 20 of the drive screw. Again, the second crank handle 156 may be rotated as needed to align the dogs of one element with the spaces between the dogs of the other. When this is accomplished, continued operation of the first crank handle 145 lowers the placement member 126 until the collet finger latches 172a snap under the shoulder 22 of the drive screw 10a. Such action by the latches 172a is caused by the bias of the collet fingers 172 to move radially outwardly. The inner surfaces of the drive screw dogs 20 are beveled. The outer surfaces of the latches 172a are also beveled. Thus, as the collet fingers 172 move downwardly within the drive screw 10a, they are first urged inwardly while the latches 172a move over the beveled surfaces of the dogs 20 leading to the shoulder 22, then catch under that shoulder.

The placement member 126 thus engages the holder 10 by the collet fingers 172 extending down within the drive screw 10a so that the latches 172a catch behind the undercut shoulder 22, and the rotary drive dogs 170 of the torque head 130 mesh with the matching dogs 20 of the drive screw, as seen in FIG. 3B. As long as such engagement is maintained, the drive screw 10a is fixed relative to the placement member 126 against both rotational as well as translational movement.

With the placement member 126 thus connected to the coupon holder 10, the second handle 156 is operated to cause the torque head 130, joined to the worm gear 148 by way of the spline collar 132, to rotate in a left-hand sense relative to the pipe P. The meshing of the dogs 170 and 20 effects an application of torque on the drive screw 10a. Thus, the drive screw is turned in the nipple threads 12a to raise the drive screw relative to the nipple 12. As the drive screw 10a is initially raised in this manner, it lifts off of the seal section 10b to the extent permitted by the longitudinal position of the retaining ring 34 on the seal section shaft 28. Once the ring 34 is contacted by the rising drive screw 10a, continued rotation of the drive screw by way of the placement member 126 results in the drive screw raising the seal section 10b. The metal-to-metal seal at the surfaces 12b and 38 is broken. Then, the seal between the packing 42 and the inner nipple surface 12c is slowly disengaged as the crank handle 156 is continued to be turned.

As the seal section 10b is pulled upwardly by the rotating drive screw 10a, the key 46 is constrained to longitudinal movement by the slot 12d. Consequently, the torque transmitted from the drive screw 10a to the seal section 10b by way of the clutch washer 44 is overridden, and the seal section does not rotate.

After the metal-to-metal seal on the surfaces 12b and 38, and the primary seal of the packing 42 and the surface 12c are both broken, fluid pressure from within the pipe P is communicated through out the interior of the landing nipple 12 and of the extractor tool 100. The pressure bypass ports 26 facilitate the communication of pressure beyond the holder 10 into the extractor tool 100. With the two bleed valves 108 and 160 closed, the pressure is contained within the extractor tool 100 by means of various seals described hereinbefore.

The ratio between the pitch of the helical gear 152 and the pitch of the threads 12a and 36 is such that many turns of the second crank handle 156 are required to advance the seal section 10b. Thus, the seal between the coupon holder 10 and the landing nipple 12 is opened slowly to allow the large pressure differential across that seal to equalize at a relatively slow rate. Consequently, the holder 10, and even the extractor tool 100 itself, is prevented from being blown out by the sudden exposure of the high pressure within the pipe P to atmospheric pressure. Furthermore, the aforementioned pitch ratio results in a large mechanical advantage in the handle 156 to not only break the sealing of the holder 10 to the landing nipple 12, but also to resist unintended upward propulsion of the holder and placement member 126.

As the second crank handle 156 is operated to raise the drive screw 10a, and eventually also the rest of the holder 10, lifting of the placement member 126 forces the rack 128 upwardly causing the first crank handle 145 to rotate. Eventually the threads 38 of the drive screw 10a are disengaged from the threads 12a of the landing nipple 12. The spline collar 132 extends downwardly along the placement member 126 a sufficient distance to ensure that the placement member and the attached drive screw 10a may be rotated to so disengage the latter from the landing nipple threads 12a. Once this has occured, the placement member 126 and the holder 10 may be more rapidly raised by operation of the first crank handle 145, without rotation of the worm gear 148. Disengagement of the spline collar 132 from the worm gear 148 occurs after the placement member 126 is moved above the position required to disengage the drive screw threads 38 from the landing nipple threads 12a.

When the placement member 126 and the holder 10 are raised, by operation of the first crank handle 145, above the ball valve 116, the ball valve is closed to seal off the inner chamber 106 from the pipe P. The bleed valve 160 is opened slowly to equalize the pressure between the chamber 106 and the surrounding atmosphere. Completion of such pressure equalization is indicated by an appropriate reading on the pressure gauge 158.

The nut 112 is then disengaged from the ball valve housing 114. The housing 104, the worm gear retainer 110 and the nut 112 are removed from the ball valve 116, exposing the inner chamber 106. The first crank handle 145 may be rotated to move the placement member 126 to expose the holder 10. The coupons 68 mounted on the holder section 10c may then be replaced. The holder section 10c may also be replaced with one featuring a shaft 62 of different length by removing the said screw 56. If desired, the placement member 126 may be advanced to expose the entire coupon holder 10, which may then be removed from the collet fingers 172 by a sharp pull. In this way, the coupon holder 10 itself may be replaced, with the new holder being pushed onto the collet fingers 172 with the holder dogs 20 meshed with the drive dogs 170.

A holder 10 according to the present invention may be mounted in a landing nipple 12 by use of the extractor tool 100. The holder 10 is pushed onto the collet fingers 172 as described, with the holder dogs 20 meshed with the drive dogs 170. The first crank handle 145 is operated to retract the placement member 126 and the holder 10 so that the holder section 10c and the coupons 68 attached thereto do not extend beyond the worm gear retainer 110. The extractor tool housing 104 is then positioned over the ball valve 116 and the nut 112 engages and is tightened on the threads of the valve housing 114.

At this point a pressure differential exists across the ball valve 16, the pressure within the inner chamber 106 being atmospheric. With the bleed valves 108 and 160 closed, the ball valve element 162 is slowly turned to break the seal between that element and the packing 164. The pressure differential across the valve element 162 is thus gradually diminished by a slow, controlled leak. As the pressure builds up above the ball valve 116, as reflected by the pressure gauge 158, the valve element 162 may continue to be turned until the passage therethrough is aligned with the inner chamber 106. The placement member 12 may then be lowered to position and anchor the holder 10 in the landing nipple 12.

The first crank handle 145 may be operated to lower the placement member 126 until the seal section key 46 contacts the top of the landing nipple threads 12a. In that configuration, the spline collar 132 has been lowered to the top of the worm gear 148, and these two elements have been meshed. Then, the torque head 130 may be rotated by means of the second crank handle 156 to rotate the drive screw 10a as the drive screw is further urged downwardly by continued rotation of the first handle 145. Torque is transmitted from the drive screw 10a to the seal section 10b by means of the clutch washer 44. With the key 46 not confined by the slot 12d, the seal section 10b rotates with the drive screw 10a. Rotation of the seal section 10b thus continues with the key 46 riding along the descending top of the nipple threads 12a until the key reaches the slot 12d. Further rotation of the seal section 10b is then prevented by the key 46 abutting the top nipple thread on the opposite side of the slot 12d. Continued rotation of the first crank handle 145 further lowers the holder 10, with seal section key 46 riding downwardly along the slot 12d, and the clutch washer 44 being overridden.

The washer 44 thus ensures that the seal section 10b is rotated relative to the nipple 12 until the seal section orienting key 46 engages the slot 12d to lock the coupons oriented within the pipe P in the direction desired. Once this orientation of holder section 10c is assured, the seal section 10b is locked against further rotation relative to the landing nipple by the key 46 passing downwardly into the slot 12d, and the clutch washer 46 is overridden.

The second crank handle 156 may be continually turned as the first crank handle 145 is operated to further lower the holder 10 into the landing nipple 12. In such case, the drive screw 10a will be rotating when its threads 36 first contact the landing nipple threads 12a. As soon as such contact is made, the threads 36 and 12a mesh and the incidental rotation of the drive screw 10a causes that element, and the attached placement member 126, to be virtually immediately drawn downwardly. This downward pull by the holder 10 is noticeable on the part of the operator turning the first crank handle 145 because the rack 128 will apply torque to the spur gear 136. Further advancement of the drive screw 10a may be effected solely by operation of the second crank handle 156. Thus, not only is the operator signaled when the drive screw threads 36 engage the landing nipple threads 12a, but such contact between the threads 36 and 12a may be effected without damage thereto.

Continued rotation of the lower crank handle 156 causes further rotation of the drive screw 10a with attendant advancement of the placement member 126 and the holder 10 downwardly relative to the landing nipple 12. Eventually, the non-rotating seal section 10b is lowered sufficiently for the packing 42 to pass within the reduced diameter surface 12c and to seat in fluid-tight engagement with that surface. Further lowering of the seal section 10b causes the seal section surface 38 to contact the landing nipple surface 12b. However, the metal-to-metal seal between the surfaces 38 and 12b of the seal section and landing nipple, respectively, is not closed until the seal section 10b is forced downwardly against the landing nipple. Such force is provided after the drive screw 10a is further rotated to advance and close the gap between its bottom surface and the seal section shoulder 32. Then, tightening the drive screw 10a in the nipple threads 12a presses the drive screw down directly against the seal section 10b, causing the surface 38 to press against the nipple surface 12b in sealing engagement. In this way, the metal-to-metal seal between the holder 10 and the nipple 12 is set without relative rotation between the sealing surfaces 38 and 12b. Sufficient pressure is applied, by way of the tightening of the drive screw in the threads 12a, to effect a high pressure fluid-tight seal between the mutually facing surfaces 12b and 38. This pressure is maintained effective due to the low pitch of the threads 12a and 36 holding the drive screw 10a in position relative to the landing nipple 12. The tightening of the drive screw 10a in the landing nipple threads 12a also serves to anchor the holder 10 to the landing nipple 12 due to the coarse, low-pitch configuration of the threads 12a and 36.

At this point, the entire holder 10 is in operating configuration, and the extractor tool 100 may be disengaged and removed. With the second crank handle 156 no longer being operated, a short, sharp turn of the first crank handle 145 in the direction to raise rack 128 will cause the collet latches 172a to ride around the shoulder 22 to release the placement member 126 from the holder 10. The upwardly facing surfaces of the collet latches 172a are tapered upwardly and inwardly as shown in the drawings to facilitate this abrupt movement around the shoulder 22, although such tapering is not sufficient to disengage the collet fingers from the drive screw 10a when the holder 10 is being lifted free of threaded engagement with the landing nipple 12.

The first crank handle 145 is continually rotated to draw the placement member 126 upwardly so that the collet fingers 172 clear the top of the landing nipple 12. The bleed valve 160 may then be opened to slowly leak the high pressure within the extractor tool 100 to the atmosphere. The double sealing by the packing 42 and the metal-to-metal seal of the surfaces 12b and 38 prevents the high pressure within the pipe P from communicating upwardly beyond the seal section 10b. When the pressure gauge 158 indicates that there is no pressure differential between the inner chamber 106 and the surrounding atmosphere, the floating nut 102 may be rotated and disengaged from the external threads 16 of the landing nipple to remove the extractor tool therefrom.

It will be appreciated from the construction described herein that the holder of the present invention may be mounted in a landing nipple oriented in any direction. Further, by appropriate selection of construction materials, particularly the resilient packing 42, the present invention may be utilized in the case of a container of pressurized fluids of extreme temperatures, either high or low.

Construction of the present invention, including the shoulder 32 to provide thrust-transmitting direct abutment between the drive screw 10a and the seal section 10b ensures that the pressure bypass ports 26 are open at all times. Further, the use of a single set screw 56 to anchor the holder section 10c to the seal section 10b in a predetermined orientation permits relatively easy and quick attachment and release of the holder section relative to the seal section.

The advantage of the lack of moving parts in the orienting device 46 attached to the seal section will be appreciated in that the possibility of jamming or obstructing the device, such as the key herein, with matter from the fluid flow within the pipe P has been virtually eliminated. Also, the position of both the key 46 and the contoured orienting surface, in the form of the slot 12d, on the low pressure side of the holder seals isolates these orientation devices from the pressurized fluid flow in the pipeline once the seals are set.

While the operation of retrieving and mounting the holder of the present invention have been described in terms of employing the extractor tool of the aforementioned copending patent application, the present invention is not limited to mounting and retrieval, under pressure conditions, by use of that particular extractor tool.

The foregoing disclosure and description of the invention is illustrative and explanatory thereof, and various changes in the size, shape and materials as well as in the details of the illustrated construction may be made within the scope of the appended claims without departing from the spirit of the invention.

I claim:

1. Apparatus for use with containers of fluid under pressure comprising:
   (a) landing means generally circumscribing a passage communicating with the interior of such a container;
   (b) holder means which may be received by said landing means;
   (c) anchor means, as part of said holder means, for anchoring said holder means to said landing means by threaded engagement of said anchor means to said landing means;
   (d) seal means, as part of said holder means, for fluid-sealing said holder means to said landing means; and
   (e) connection means, for coupling said seal means to said anchor means while permitting rotational movement and limited translational movement between said seal means and said anchor means, including a projection of said seal means into at least a portion of said anchor means and retaining means cooperating with said projection and with said anchor means to retain said seal means so coupled to said anchor means.

2. Apparatus as defined in claim 1 further comprising clutch means, for imparting torque between said anchor means and said seal means, comprising generally annular compression means confined between said anchor means and said seal means whereby frictional forces may be effected between said compression means and at least one of said anchor means and said seal 3. Apparatus as defined in claim 2 wherein said generally annular compression means comprises wavy washer means.

4. Apparatus as defined in claim 2 wherein said generally annular compression means generally circumscribes said seal means projection.

5. Apparatus as defined in claim 2 further comprising abutment means for communicating thrust between said anchor means and said seal means, and for limiting the compression of said generally annular compression means between said anchor means and said seal means.

6. Apparatus as defined in claim 5 wherein:
   (a) said abutment means comprises a generally annular shoulder as part of said seal means, generally circumscribing said seal means projection;
   (b) said generally annular compression means comprises a wavy washer generally circumscribing said shoulder; and
   (c) relative translational movement of said seal means and said anchor means toward each other is limited by said shoulder abutting said anchor means thereby limiting the compression of said wavy washer.

7. Apparatus as defined in claim 2 further comprising orientation means for automatically orienting said seal section relative to said landing means when said landing means has received said holder means.

8. Apparatus as defined in claim 1 further comprising:
   (a) contoured surface means as part of said landing means; and
   (b) orientation means, fixed relative to said seal means, for cooperating with said contoured surface means for orienting said seal means relative to said landing means.

9. Apparatus as defined in claim 8:
   (a) further comprising at least one seal element, as part of said seal means, for cooperating with said landing means for fluid-sealing said holder means to said landing means; and
   (b) wherein, when said holder means is so fluid-sealed to said landing means, said orientation means is thereby fluid-sealed from such fluid under pressure.

10. Apparatus as defined in claim 8 further comprising mounting means, as part of said holder means, for supporting equipment for placement within said container, and wherein said mounting means is releaseably attached to said seal means such that said mounting means is automatically oriented relative to said landing means as said seal means is so oriented relative to said landing means.

11. Apparatus as defined in claim 1 further comprising:
(a) mounting means, as part of said holder means, for supporting equipment for placement within said container; and
(b) means for selectively releaseably attaching said mounting means to said seal means.

12. Apparatus as defined in claim 11 further comprising insulation means for isolating said mounting means from direct contact with such equipment while permitting such equipment to be mounted on said mounting means.

13. Apparatus for use with containers of fluid under pressure comprising:
(a) landing means generally circumscribing a passage communicating with the interior of such a container;
(b) holder means which may be received by said landing means;
(c) anchor means, as part of said holder means, for anchoring said holder means to said landing means by threaded engagement of said anchor means to said landing means;
(d) seal means, as part of said holder means, for fluid-sealing said holder means to said landing means;
(e) contoured surface means as part of said landing means; and
(f) orientation means, fixed relative to said seal means, for cooperating with said contoured surface means for orienting said seal means relative to said landing means.

14. Apparatus as defined in claim 13:
(a) further comprising at least one seal element, as part of said seal means, for cooperating with said landing means for fluid-sealing said holder means to said landing means; and
(b) wherein, when said holder means is so fluid-sealed to said landing means, said orientation means is thereby fluid-sealed from such fluid under pressure.

15. Apparatus as defined in claim 13 further comprising mounting means, as part of said holder means, for supporting equipment for placement within said container, and wherein said mounting means is releaseably attached to said seal means such that said mounting means is automatically oriented relative to said landing means as said seal means is so oriented relative to said landing means.

16. Apparatus as defined in claim 13 further comprising:
(a) mounting means, as part of said holder means, for supporting equipment for placement within said container; and
(b) means for selectively releaseably attaching said mounting means to said seal means.

17. Apparatus as defined in claim 16 further comprising insulation means for isolating said mounting means from direct contact with such equipment while permitting such equipment to be mounted on said mounting means.

18. Apparatus as defined in claim 13 further comprising clutch means, for imparting torque between said anchor means and said seal means, comprising generally annular compression means confined between said anchor means and said seal means whereby frictional forces may be effected between said compression means and at least one of said anchor means and said seal means.

19. Apparatus as defined in claim 18 wherein said generally annular compression means comprises wavy washer means.

20. Apparatus as defined in claim 18 further comprising abutment means for communicating thrust between said anchor means and said seal means, and for limiting the compression of said generally annular compression means between said anchor means and said seal means.

21. Apparatus as defined in claim 18:
(a) further comprising at least one seal element, as part of said seal means, for cooperating with said landing means for fluid-sealing said holder means to said landing means; and
(b) wherein, when said holder means is so fluid-sealed to said landing means, said orientation means is thereby fluid-sealed from such fluid under pressure.

22. Apparatus as defined in claim 18 further comprising connection means, for coupling said seal means to said anchor means while permitting rotational movement and limited translational movement between said seal means and said anchor means, including a projection of said seal means into at least a portion of said anchor means and retaining means cooperating with said projection and with said anchor means to retain said seal means so coupled to said anchor means.

23. Apparatus as defined in claim 22 further comprising abutment means for communicating thrust between said anchor means and said seal means, and for limiting the compression of said generally annular compression means between said anchor means and said seal means.

24. Apparatus as defined in claim 23 wherein:
(a) said abutment means comprises a generally annular shoulder as part of said seal means, generally circumscribing said seal means projection;
(b) said generally annular compression means comprises a wavy washer generally circumscribing said shoulder; and
(c) relative translational movement of said seal means and said anchor means toward each other is limited by said shoulder abuting said anchor means thereby limiting the compression of said wavy washer.

25. Apparatus as defined in claim 22 wherein said generally annular compression means generally circumscribes said seal means projection.

26. Apparatus for use with containers of fluid under pressure comprising:
(a) landing means generally circumscribing a passage communicating with the interior of such a container;
(b) holder means which may be received by said landing means;
(c) anchor means, as part of said holder means, for anchoring said holder means to said landing means by threaded engagement of said anchor means to said landing means;
(d) seal means, as part of said holder means, for fluid-sealing said holder means to said landing means; and
(e) clutch means, for imparting torque between said anchor means and said seal means, comprising generally annular compression means confined between said anchor means and said seal means whereby frictional forces may be effected between said compression means and at least one of said anchor means and said seal means.

27. Apparatus as defined in claim 26 further comprising:
(a) connection means, for coupling said seal means to said anchor means while permitting rotational movement and limited translational movement between said seal means and said anchor means, including a projection of said seal means into at least a portion of said anchor means and retaining means cooperating with said projection and with said anchor means to retain said seal means so coupled to said anchor means;
(b) contoured surface means as part of said landing means;
(c) orientation means, fixed relative to said seal means, for cooperating with said contoured surface means for orienting said seal means relative to said landing means; and
(d) mounting means, as part of said holder means, for supporting equipment for placement within said container, and wherein said mounting means is releaseably attached to said seal means such that said mounting means is automatically oriented relative to said landing means as said seal means is so oriented relative to said landing means.

28. Apparatus as defined in claim 27 further comprising abutment means for communicating thrust between said anchor means and said seal means, and for limiting the compression of said generally annular compression means between said anchor means and said seal means.

29. Apparatus as defined in claim 28 wherein:
(a) said abutment means comprises a generally annular shoulder as part of said seal means, generally circumscribing said seal means projection;
(b) said generally annular compression means comprises a wavy washing generally circumscribing said shoulder; and
(c) relative translational movement of said seal means and said anchor means toward each other is limited by said shoulder abuting said anchor means thereby limiting the compression of said wavy washer.

30. Apparatus as defined in claim 29:
(a) further comprising at least one seal element, as part of said seal means, for cooperating with said landing means for fluid-sealing said holder means to said landing means; and
(b) wherein, when said holder means is so fluid-sealed to said landing means, said orientation means is thereby fluid-sealed from such fluid under pressure.

31. Apparatus as defined in claim 27 wherein said generally annular compression means comprises wavy washer means.

32. Apparatus as defined in claim 26 wherein said generally annular compression means comprises wavy washer means.

33. Apparatus as defined in claim 26 further comprising orientation means for automatically orienting said seal section relative to said landing means when said landing means has received said holder means.

34. Apparatus as defined in claim 26 further comprising:
(a) mounting means, as part of said holder means, for supporting equipment for placement within said container; and
(b) means for selectively releaseably attaching said mounting means to said seal means.

35. Apparatus as defined in claim 34 or, in the alternative, as defined in claim 27 further comprising insulation means for isolating said mounting means for direct contact with such equipment while permitting such equipment to be mounted on said mounting means.

36. Apparatus for use with containers of fluid under pressure comprising:
(a) landing means generally circumscribing a passage communicating with the interior of such a container;
(b) holder means which may be received by said landing means;
(c) anchor means, as part of said holder means, for anchoring said holder means to said landing means by threaded engagement of said anchor means to said landing means;
(d) seal means, as part of said holder means, including at least one seal element for cooperating with said landing means for fluid-sealing said holder means to said landing means; and
(e) orientation means for automatically orienting said seal means relative to said landing means, such that, when said holder means is so fluid-sealed to said landing means, said orientation means is thereby fluid-sealed from such fluid under pressure.

37. Apparatus as defined in claim 36 further comprising clutch means, for imparting torque between said anchor means and said seal means, comprising generally annular compression means confined between said anchor means and said seal means whereby frictional forces may be effected between said compression means and at least one of said anchor means and said seal means.

38. Apparatus as defined in claim 37 further comprising connection means, for coupling said seal means to said anchor means while permitting rotational movement and limited translational movement between said seal means and said anchor means, including a projection of said seal means into at least a portion of said anchor means and retaining means cooperating with said projection and with said anchor means to retain said seal means so coupled to said anchor means.

39. Apparatus as defined in claim 38 wherein said generally annular compression means generally circumscribes said seal means projection.

40. Apparatus as defined in claim 39 wherein said generally annular compression means comprises wavy washer means.

41. Apparatus as defined in claim 36 further comprising mounting means, as part of said holder means, for supporting equipment for placement within said container, and wherein said mounting means is releaseably attached to said seal means such that said mounting means is automatically oriented relative to said landing means as said seal means is so oriented relative to sand landing means.

42. Apparatus as defined in claim 36 further comprising:
(a) mounting means, as part of said holder means, for supporting equipment for placement within said container; and
(b) means for selectively releaseably attaching said mounting means to said seal means.

43. Apparatus as defined in claim 42 further comprising insulation means for isolating said mounting means for direct contact with such equipment while permitting such equipment to be mounted on said mounting means.

44. Apparatus as defined in claim 26 further comprising abutment means for communicating thrust between said anchor means and said seal means, and for limiting the compression of said generally annular compression means between said anchor means and said seal means.

45. Apparatus as defined in claim 12 wherein said insulation means further comprises shoulder means cooperating with means on such equipment for holding said equipment fixed relative to said mounting means.

46. Apparatus as defined in claim 17 wherein said insulation means further comprises shoulder means cooperating with means on such equipment for holding said equipment fixed relative to said mounting means.

47. Apparatus as defined in claim 35 wherein said insulation means further comprises shoulder means cooperating with means on such equipment for holding said equipment fixed relatie to said mounting means.

48. Apparatus as defined in claim 45 wherein said insulation means further comprises shoulder means cooperating with means on such equipment for holding said equipment fixed relative to said mounting means.

* * * * *